US009127321B2

(12) United States Patent
Engelthaler et al.

(10) Patent No.: US 9,127,321 B2
(45) Date of Patent: Sep. 8, 2015

(54) METHOD OF DETECTING *COCCIDIOIDES* SPECIES

(75) Inventors: David Engelthaler, Flagstaff, AZ (US); Elizabeth Driebe, Flagstaff, AZ (US); Paul Keim, Flagstaff, AZ (US)

(73) Assignees: The Translational Genomics Research Institute, Phoenix, AZ (US); The Arizona Board of Regents on Behalf of Northern Arizona University, Flagstaff, AZ (US)

( * ) Notice: Subject to any disclaimer, the term of this patent is extended or adjusted under 35 U.S.C. 154(b) by 1007 days.

(21) Appl. No.: 13/267,865

(22) Filed: Oct. 6, 2011

(65) Prior Publication Data

US 2012/0264135 A1 Oct. 18, 2012

Related U.S. Application Data

(60) Provisional application No. 61/390,500, filed on Oct. 6, 2010.

(51) Int. Cl.
*C12Q 1/68* (2006.01)

(52) U.S. Cl.
CPC .................................... *C12Q 1/6895* (2013.01)

(58) Field of Classification Search
None
See application file for complete search history.

(56) References Cited

U.S. PATENT DOCUMENTS

| | | | | |
|---|---|---|---|---|
| 5,922,855 | A * | 7/1999 | Liskay et al. | 536/23.5 |
| 6,235,890 | B1 * | 5/2001 | Morrison et al. | 536/24.33 |
| 2002/0028487 | A1 * | 3/2002 | La Thangue et al. | 435/69.1 |
| 2002/0061545 | A1 * | 5/2002 | Choi et al. | 435/7.34 |
| 2003/0050470 | A1 * | 3/2003 | An et al. | 536/24.3 |
| 2004/0023207 | A1 * | 2/2004 | Polansky | 435/5 |
| 2004/0209241 | A1 * | 10/2004 | Hermanson et al. | 435/5 |
| 2007/0026452 | A1 * | 2/2007 | Matalon et al. | 435/6 |

OTHER PUBLICATIONS

Applied Biosystems Standard Dye Sets for Genotyping Applications. [online] [retrieved on Dec. 5, 2014] retrieved from: http://faculty.georgetown.edu/hamiltm1/DNA_Fragment_Sizing_Facility_files/ABI%20Dye%20Se%20card.pdf (2 pages).*

BHQplus® Probes. [online] [retrieved on Dec. 5, 2014] retrieved from: https://www.biosearchtech.com/bhqplus (2 pages).*

Matrix Standards Set DS-02 (Applied Biosystems). Sep. 23, 2010 (2 pages).*

Fluorophore & BHQ® Dye Selection Chart. [online] [retrieved on Dec. 5, 2014] retrieved from: http://www.biosearchtech.com/assets/bti_bhq_selectionchart.pdf (2 pages).*

2014 Procedures for subject matter eligibility analysis of claims reciting or involving laws of nature/natural principles, natural phenomena, and/or natural products. United States Patent & Trademark Office, Mar. 4, 2014 (19 pages).*

Daniels et al. Development of a quantitative TaqMan-PCR assay and feasibility of atmospheric collection for *Coccidioides* immitis for ecological studies. U.S. Department of Energy, Lawrence Livermore National Laboratory, Feb. 1, 2002 (25 pages).*

Wang, G. Identification of *Coccidioides* by real-time PCR with a Taqman probe. Master's Thesis, San Francisco State University, Aug. 2007 (46 pages).*

Binnicker et al. Detection of *Coccidioides* species in clinical specimens by real-time PCR. Journal of Clinical Microbiology 45:173-178, Jan. 2007.*

GenBank GI 73912438 [online] Aug. 30, 2005 [retrieved on Dec. 8, 2014] retrieved from http://www.ncbi.nlm.nih.gov/nuccore/73912438?sat=34&satkey=2831594.*

GenBank GI 73912439 [online] Aug. 30, 2005 [retrieved on Dec. 8, 2014] retrieved from http://www.ncbi.nlm.nih.gov/nuccore/73912439?sat=34&satkey=2831595.*

GenBank GI 73912440 [online] Aug. 30, 2005 [retrieved on Dec. 8, 2014] retrieved from http://www.ncbi.nlm.nih.gov/nuccore/73912440?sat=34&satkey=2831596.*

GenBank GI 73912441 [online] Aug. 30, 2005 [retrieved on Dec. 8, 2014] retrieved from http://www.ncbi.nlm.nih.gov/nuccore/73912441?sat=34&satkey=2831597.*

GenBank GI 73912442 [online] Aug. 30, 2005 [retrieved on Dec. 8, 2014] retrieved from http://www.ncbi.nlm.nih.gov/nuccore/73912442?sat=34&satkey=2831598.*

GenBank GI 73912443 [online] Aug. 30, 2005 [retrieved on Dec. 8, 2014] retrieved from http://www.ncbi.nlm.nih.gov/nuccore/73912443?sat=34&satkey=2831599.*

GenBank GI 73912444 [online] Aug. 30, 2005 [retrieved on Dec. 8, 2014] retrieved from http://www.ncbi.nlm.nih.gov/nuccore/73912444?sat=34&satkey=2831600.*

GenBank GI 73912445 [online] Aug. 30, 2005 [retrieved on Dec. 8, 2014] retrieved from http://www.ncbi.nlm.nih.gov/nuccore/73912445?sat=34&satkey=2831601.*

GenBank GI 73912446 [online] Aug. 30, 2005 [retrieved on Dec. 8, 2014] retrieved from http://www.ncbi.nlm.nih.gov/nuccore/73912446?sat=34&satkey=2831602.*

GenBank GI 73912447 [online] Aug. 30, 2005 [retrieved on Dec. 8, 2014] retrieved from http://www.ncbi.nlm.nih.gov/nuccore/73912447?sat=34&satkey=2831603.*

GenBank GI 73912448 [online] Aug. 30, 2005 [retrieved on Dec. 8, 2014] retrieved from http://www.ncbi.nlm.nih.gov/nuccore/73912448?sat=34&satkey=2831604.*

GenBank GI 73912449 [online] Aug. 30, 2005 [retrieved on Dec. 8, 2014] retrieved from http://www.ncbi.nlm.nih.gov/nuccore/73912449?sat=34&satkey=2831605.*

GenBank GI 73912450 [online] Aug. 30, 2005 [retrieved on Dec. 8, 2014] retrieved from http://www.ncbi.nlm.nih.gov/nuccore/73912450?sat=34&satkey=2831606.*

GenBank GI 73912451 [online] Aug. 30, 2005 [retrieved on Dec. 8, 2014] retrieved from http://www.ncbi.nlm.nih.gov/nuccore/73912451?sat=34&satkey=2831607.*

GenBank GI 73912452 [online] Aug. 30, 2005 [retrieved on Dec. 8, 2014] retrieved from http://www.ncbi.nlm.nih.gov/nuccore/73912452?sat=34&satkey=2831608.*

(Continued)

*Primary Examiner* — Samuel Woolwine

(57) ABSTRACT

The present invention provides methods and kits that may be used to detect and quantify the presence of *Coccidioides* species. The methods include quantification PCR assays, and the kits and compositions include oligonucleotides used as primers and probes.

21 Claims, 2 Drawing Sheets

(56) References Cited

OTHER PUBLICATIONS

GenBank GI 73912453 [online] Aug. 30, 2005 [retrieved on Dec. 8, 2014] retrieved from http://www.ncbi.nlm.nih.gov/nuccore/73912453?sat=34&satkey=2831609.*

GenBank GI 73912454 [online] Aug. 30, 2005 [retrieved on Dec. 8, 2014] retrieved from http://www.ncbi.nlm.nih.gov/nuccore/73912454?sat=34&satkey=2831610.*

GenBank GI 73912455 [online] Aug. 30, 2005 [retrieved on Dec. 8, 2014] retrieved from http://www.ncbi.nlm.nih.gov/nuccore/73912455?sat=34&satkey=2831611.*

GenBank GI 73912456 [online] Aug. 30, 2005 [retrieved on Dec. 8, 2014] retrieved from http://www.ncbi.nlm.nih.gov/nuccore/73912456?sat=34&satkey=2831612.*

Lo, Y.M. Methods in Molecular Biology 336, Humana Press (2006); front matter and pp. 1-10 (21 total pages).*

SantaLucia, J. Methods in Molecular Biology 402, Humana Press (2007); front matter and pp. 3-33 (40 total pages).*

Eurogentec [online] May 24, 2005 [retrieved on Nov. 3, 2013] retrieved from http://web.archive.org/web/20050524042658/http://www.gene-quantification.de/eurogentec-RT-PCR-booklet.pdf.*

* cited by examiner

METHOD OF DETECTING *COCCIDIOIDES* SPECIES

CROSS REFERENCE TO RELATED APPLICATIONS

This application claims the priority of U.S. provisional applications entitled METHOD OF DETECTING *COCCIDIOIDES* SPECIES, with application No. 61/390,500, filed on Oct. 6, 2010, which is hereby incorporated by reference in its entirety.

FIELD OF THE INVENTION

The present invention provides methods and kits for specifically detecting and quantifying *Coccidioides* in a sample.

BACKGROUND OF THE INVENTION

Coccidioidomycosis is caused by infection with *Coccidioides immitis* or *C. posadasii. Coccidioides immitis* and *C. posadasii* are the fungal etiologic agents of coccidioidomycosis (aka Valley Fever) and are endemic to arid soils of the southwest United States, as well as parts of Mexico, and Central and South America. Primary hosts acquire *Coccidioides* via inhalation of aerosolized arthroconidia upon soil disruption. Coccidioidomycosis most commonly causes a progressive pulmonary infection in humans and other vertebrate hosts but also can disseminate to other body parts including the skin, brain, bone, and meninges. This disseminated secondary coccidioidomycosis often is severe and can result in patient death (See Reference 3). However, in cases where infection is resolved patients usually acquire a specific and lifelong immunity to the fungus.

Coccidioidomycosis infection rates have increased dramatically in the last decade with the state of Arizona documenting the number of reported cases per 100,000 people having increased from 20.8 in 1997 to 86.1 in 2006. A potential causes for this increase include influxes of immunologically naïve individuals into Arizona. A significant number of individuals from outside the *Coccidioides* endemic region migrate annually to the desert southwest and are at greater risk for development of coccidioidomycosis, even after return to their respective homes. These infections, therefore, are likely to escape or confound diagnosis in non-endemic regions.

While Real Time PCR based assays have been developed that help clinicians identify *Coccidioides* as a cause of illness, these assays do not accurately quantify the load of *Coccidioides* organisms in an infection. Population influx in *Coccidioides*-endemic areas may contribute to rate of infection increases not only because there are additional individuals relocating to these areas but also because there is increased new home construction in virgin desert areas, and subsequent soil disturbances.

BRIEF SUMMARY OF THE INVENTION

Provided herein is a method of determining the presence or absence of *Coccidioides* in a DNA-containing sample comprising the steps of adding a first oligonucleotide capable of binding SEQ ID NO. 4 to a mixture comprising the DNA-containing, wherein the first oligonucleotide includes a sequence selected from the group consisting of SEQ ID NO. 2 and SEQ ID NO. 3; subjecting the mixture to conditions that allow amplification of nucleic acid amplification comprising the first oligonucleotide; obtaining a result indicating nucleic acid amplification comprising the first oligonucleotide; and determining the presence or absence of *Coccidioides* in the DNA-containing sample based on the result. In the general method, said result may comprise a Ct value.

In one example, the first oligonucleotide of the method is capable of hybridizing with complements of SEQ ID NO. 2, then the method further comprises adding a second oligonucleotide that is capable of hybridizing with complements of SEQ ID NO. 3 to the mixture. Or, if the first oligonucleotide is capable of hybridizing with complements of SEQ ID NO. 3, then the method preferably further comprises adding a second oligonucleotide that is capable of hybridizing with complements of SEQ ID NO. 2 to the mixture. The general method may further comprise adding a third oligonucleotide to the mixture, and this third oligonucleotide binds to its complement included in the amplification products by the first and second oligonucleotides. In one example, the third oligonucleotide includes SEQ ID NO. 4. In the general method, at least one of the first and the second oligonucleotides comprises a label. In one example, the label comprises a fluorescent label selected from the group consisting of FAM™ (fluorescein), dR110 (dichloro-substituted rhodamine 110), 5-FAM™ (5-carboxyfluorescein), 6FAM™ (6-carboxyfluorescein), dR6G (dichloro-substituted rhodamine 6G), JOE™ (4-5-dichloro-carboxyfluorescein), HEX™ (hexachloro-fluorescein), VIC®, TET™ (6-carboxy-1,4-dichloro-2',7'-dichloro-fluorescein), dTAMRA™ (dichloro-substituted carboxytetramethylrhodamine), TAMRA™ (carboxytetramethylrhodamine), NED™, dROX™ (dichloro-substituted 6-carboxyl-X-rhodamine), PET®, BHQ®, CAL-Fluor® Gold 540 (diisopropyl-phosphoramidous acid 2-cyano-ethyl ester 1-[2-(6-ethylamino-2,7-dimethyl-3-oxo-3H-xanthen-9-yl)-benzoyl]-piperidin-4-yl ester), and LIZ®. In another example, the third oligonucleotide in the general method may comprise a fluorescent label selected from the group consisting of FAM™ (fluorescein), dR110 (dichloro-substituted rhodamine 110), 5-FAM™ (5-carboxyfluorescein), 6FAM™ (6-carboxyfluorescein), dR6G (dichloro-substituted rhodamine 6G), JOE™ (4-5-dichloro-carboxyfluorescein), HEX™ (hexachloro-fluorescein), VIC®, TET™ (6-carboxy-1,4-dichloro-2',7'-dichloro-fluorescein), dTAMRA™ (dichloro-substituted carboxytetramethylrhodamine), TAMRA™ (carboxytetramethylrhodamine), NED™, dROX™ (dichloro-substituted 6-carboxyl-X-rhodamine), PET®, BHQ®, CAL-Fluor® Gold 540 (diisopropyl-phosphoramidous acid 2-cyano-ethyl ester 1-[2-(6-ethylamino-2,7-dimethyl-3-oxo-3H-xanthen-9-yl)-benzoyl]-piperidin-4-yl ester), and LIZ®. The step of receiving the DNA-containing sample of the general method may further comprise the step of isolating DNA from the DNA-containing sample. Such a sample may comprise an environmental sample. Alternatively, the sample is derived from a subject, such as a human, a companion animal, or a livestock animal.

Provided herein also is a method of quantifying *Coccidioides* in a DNA-containing sample comprising the steps of: adding a first and a second oligonucleotide capable of binding SEQ ID NO. 5 to a first mixture comprising the DNA-containing sample, wherein the first oligonucleotide differs from the second oligonucleotide; adding a fourth and fifth oligonucleotide to a second mixture comprising nucleic acid having SEQ ID NO: 1 or SEQ ID NO. 6, wherein the fourth and fifth oligonucleotide differs from one another and each includes SEQ ID NO: 7 and SEQ ID NO: 8; subjecting the first and the second mixture to conditions that allow nucleic acid amplification; receiving a first result from said nucleic amplification of said first mixture and a second result from said nucleic amplification of said second mixture; and comparing said first result with said second result to thereby quantify *Coccidioides* In said method, the first and the second result may comprise a Ct value. In one example, the first oligonucleotide of the general method is capable of hybridizing with complements of SEQ ID NO. 2, and the second oligonucleotide is capable of hybridizing with complements of SEQ ID NO. 3, under stringent conditions. In another example, the first oligonucleotide is capable of hybridizing with complements of SEQ ID NO. 3, and the second oligonucleotide is capable of hybridizing with complements of SEQ ID NO. 2, under stringent conditions. Further, the first and the second result in the general method may be a Ct value. In the general method, the first oligonucleotide may include SEQ ID NO. 2, and thus the method further comprises adding a second oligonucleotide that includes SEQ ID NO. 3 to the mixture. Alternatively, the first oligonucleotide may include SEQ ID NO. 3, and thus the method further comprises adding a second oligonucleotide that includes SEQ ID NO. 2 to the mixture. In some other example, the general method further comprises a step of adding a third oligonucleotide to the mixture, wherein the third oligonucleotide binds to its complement included in the amplification products by the first and second oligonucleotides. The third oligonucleotide may include SEQ ID NO. 4. In the general method, at least one of the first and the second oligonucleotides comprises a label. In some example, the label is a fluorescent label selected from the group consisting of FAM™ (fluorescein), dR110 (dichloro-substituted rhodamine 110), 5-FAM™ (5-carboxyfluorescein), 6FAM™ (6-carboxyfluorescein), dR6G (dichloro-substituted rhodamine 6G), JOE™ (4-5-dichloro-carboxyfluorescein), HEX™ (hexachloro-fluorescein), VIC®, TET™ (6-carboxy-1,4-dichloro-2',7'-dichloro-fluorescein), dTAMRA™ (dichloro-substituted carboxytetramethylrhodamine), TAMRA™ (carboxytetramethylrhodamine), NED™, dROX™ (dichloro-substituted 6-carboxyl-X-rhodamine), PET®, BHQ®, CAL-Fluor® Gold 540 (diisopropyl-phosphoramidous acid 2-cyano-ethyl ester 1-[2-(6-ethylamino-2,7-dimethyl-3-oxo-3H-xanthen-9-yl)-benzoyl]-piperidin-4-yl ester), and LIZ®. In other example, the third oligonucleotide of the method comprises a fluorescent label selected from the group consisting of FAM™ (fluorescein), dR110 (dichloro-substituted rhodamine 110), 5-FAM™ (5-carboxyfluorescein), 6FAM™ (6-carboxyfluorescein), dR6G (dichloro-substituted rhodamine 6G), JOE™ (4-5-dichloro-carboxyfluorescein), HEX™ (hexachloro-fluorescein), VIC®, TET™ (6-carboxy-1,4-dichloro-2',7'-dichloro-fluorescein), dTAMRA™ (dichloro-substituted carboxytetramethylrhodamine), TAMRA™ (carboxytetramethylrhodamine), NED™, dROX™ (dichloro-substituted 6-carboxyl-X-rhodamine), PET®, BHQ®, CAL-Fluor® Gold 540 (diisopropyl-phosphoramidous acid 2-cyano-ethyl ester 1-[2-(6-ethylamino-2,7-dimethyl-3-oxo-3H-xanthen-9-yl)-benzoyl]-piperidin-4-yl ester), and LIZ®. The step of receiving the DNA-containing sample of the method may further comprise the step of isolating DNA from the DNA-containing sample. The sample for the method may comprise an environmental sample. Or else, the sample may be derived from a subject selected from a human, a companion animal, and a livestock animal.

Further provided herein is a kit that facilitates the detection of *Coccidioides* in a sample. The kit comprises: a first oligonucleotide capable of binding to SEQ ID NO. 5; and an indication of a result that signifies that the sample contains *Coccidioides*, wherein the first oligonucleotide is capable of hybridizing with sequence selected from the group consisting of SEQ ID NO. 2, SEQ ID NO. 3. In one example, the first oligonucleotide of the kit is capable of hybridizing with complements of SEQ ID NO. 2, and the kit further comprises a second oligonucleotide capable of hybridizing with complements of SEQ ID NO. 3, under stringent conditions. In another example, the first oligonucleotide of the kit is capable of hybridizing with complements of SEQ ID NO. 3, and the kit further comprises a second oligonucleotide capable of hybridizing with complements of SEQ ID NO. 2, under stringent conditions. In some embodiment of the kit, the kit may further comprise a third oligonucleotide including SEQ ID NO. 4. The kit may also comprise a device to be used in collecting a sample. In one example, the result referred in the kit comprises a Ct value, whereas the indication comprised in the kit may comprises a positive control, a writing, or an amplification plot. In one particular embodiment, the kit may further comprise a construct comprising a sequence selected from SEQ ID NO. 5 and SEQ ID NO. 6; wherein the construct is provided at a first known concentration; wherein the construct is useful for *Coccidioides* quantification in a sample. In some preferred forms of the invention, the construct at a second known concentration may also be provided. When there is a plurality of construct with known concentrations in a series dilution, the kit may further comprise an indication of a dilution scheme.

DETAILED DESCRIPTION OF THE INVENTION

Figure 1:
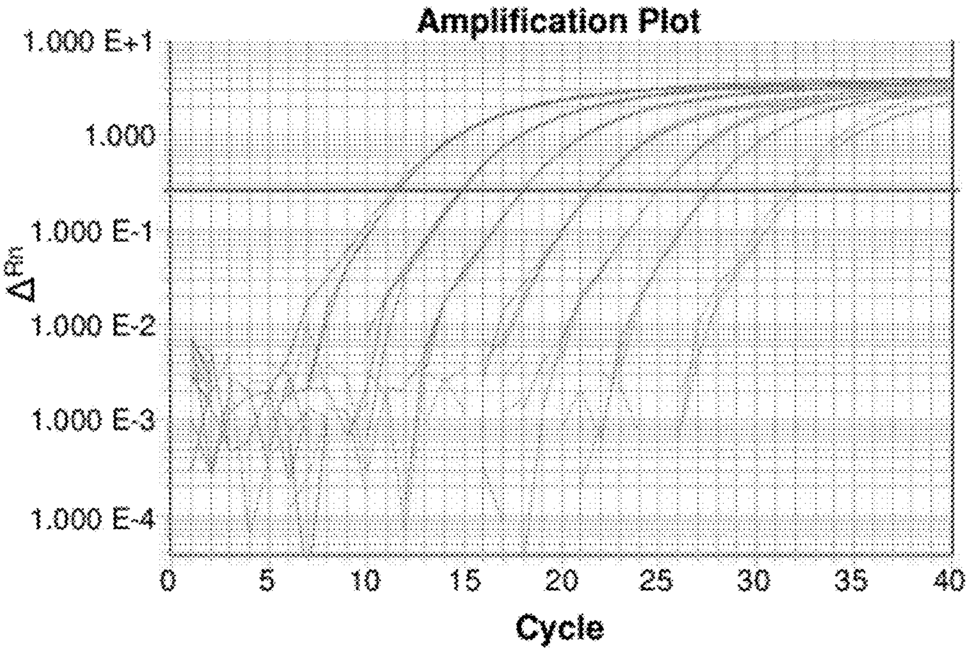
FIG. 1 depicts an amplification plot of a typical standard set using a series diluted samples containing DNA of known concentration.

This invention provides genetic signatures specific to *Coccidioides* sp, including *Coccidioides immitis* and *C. posadasii*. A real-time quantitative Polymerase Chain Reaction (qPCR) based assay, providing a straightforward, highly sensitive, specific assay system for rapidly quantifying *Coccidioides* in a sample is provided based on the signatures disclosed herein. The present invention discloses assays, methods and kits designed to detect and quantify total *Coccidioides* sp in a sample and is therefore useful in many aspects.

I. Species or Strain Specific Sequences

Species or strain specific sequences are sequences unique to the species or strain, that is, not shared by other previously characterized species or strains. The species specific sequences identified in *Coccidioides immitis* and *C. posadasii* that are species specific often differs only by a single nucleotide, which is called SNP (single nucleotide polymorphism). The strain specific SNP, is also called allelic identification herein, signifies the identity of *Coccidioides immitis* or *C. posadasii*. The concept of "allele" or "allelic" is detailed below.

When a particular species or strain specific sequence is identified, probes or primers may be designed based on any part of that sequence. The probes or primers may also be the entirety of that sequence. The primers or probes designed according to particular species or strain sequence, or alleles thereof, may also be represented in degenerate form, or comprises chemically modified nucleic acids, or any other components that facilitate the identification of the identifying sequence of a strain or species. The concept of a sequence identified to be specific to a species or strain further encompasses nucleic acid sequences that are less than 100% identical to the specific sequence, but are still capable of specifically detecting the species or strain. Note that in a nucleic acid sequence, T or U may be used interchangeably depending on whether the nucleic acid is DNA or RNA. A sequence having less than 60% 70%, 80%, 90%, 95%, 99% or 100% identity to the identifying sequence or allele thereof may still be encompassed by the invention if it is capable of binding to its complementary sequence and/or facilitating nucleic acid amplification of a desired target sequence. An allele includes any form of a particular nucleic acid that may be recognized as a form of existence of a particular nucleic acid on account of its location, sequence, modification, or any other characteristics that may identify it as being a particular existing form of that particular nucleic acid.

Alleles include, but need not be limited to, forms of a nucleic acid that include point mutations, deletions, single nucleotide polymorphisms (SNPs), inversions, translocations, heterochromatic insertions, and differentially methylated sequences relative to a reference gene, whether alone or in combination. When a particular nucleic acid is a gene, the allele of this particular gene may or may not produce a functional protein; the functional protein thereof may or may not comprise a silent mutation, or frame-shift mutation. The different alleles of a particular gene may each produce a protein with altered function, localization, stability, dimerization, or protein-protein interaction; and may have overexpression, underexpression or no expression; may have altered temporal or spacial expression specificity. The presence or absence of an allele may be detected through the use of any process known in the art, including using primers and probes designed accordingly for PCR, sequencing, hybridization analyses. An allele may also be called a mutation or a mutant. An allele may be compared to another allele that may be termed a wild type form of an allele. In some cases, the wild type allele is more common than the mutant.

The term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, i.e., in the presence of nucleotides and an inducing agent such as DNA polymerase and at a suitable temperature and pH. The primer is preferably single-stranded for maximum efficiency in amplification. Alternatively, the primer is first treated to ensure that it is single-stranded before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method. Oligonucleotides, such as a probe or primer, containing a sequence complementary to a sequence specific to a *Coccidioides* species or strain will typically not hybridize to the corresponding portion of the genome of other species or strains under stringent conditions. Understood by the skilled in the art, for example, a high stringent hybridization conditions is equivalent to: 5×SSPE, 0.5% SDS, 5×Denhardt's reagent and 100 μg/ml denatured salmon sperm DNA at 42° C. followed by washing in a solution comprising 0.1×SSPE, 1.0% SDS at 42° C. when a probe of about 500 nucleotides in length is employed, and washed with 2×SSC, 0.1% SDS followed by 0.1×SSC, 0.1% SDS. Stringent conditions in PCR reaction may be controlled by temperature, the concentration of certain salt in the buffer.

The concept of oligonucleotides includes any DNA or RNA molecule of two or more nucleotides, whether from a natural source, chemically synthesized, or produced through DNA replication, reverse transcription, or a combination thereof. A nucleotide is an individual deoxyribonucleotide or ribonucleotide base. Examples of nucleotides include but are not limited to: adenine, thymine, guanine, cytosine, and uracil, which may be abbreviated as A, T, G, C, or U in representations of oligonucleotide sequence. The length of the oligonucleotide depends on how the oligonucleotide will be used. One skilled in the art would understand the approximate length of oligonucleotide necessary in any given method. Depending on the method, an oligonucleotide may be 1 to 1000 bases in length. In other methods, it may be 5 to 500 bases in length, 5 to 100 bases in length, 5 to 50 bases in length, or 10 to 30 bases in length.

Primers and probes designed based on strain specific genes, allelic discriminative nucleic acid, or alleles thereof, are often used to screen samples to specifically and selectively detect the presence or absence of a particular species or strain. The detection using primers and probes may be through various methods including PCR-based (polymerase chain reaction-based) methods such as real-time PCR, quantitative PCR, quantitative real time PCR; allele specific ligation; comparative genomic hybridization; sequencing; and other methods known in the art. One aspect of the present invention provides primers based on *Coccidioides* specific sequence for quantitative PCR assays comprising one or more specific primer sets and probes to detect the presence of *Coccidioides*.

As to probes, they may be used for single probe analysis or multiplex probe/primer combined Real Time and quantitative PCR (qPCR) analysis. Oligonucleotide probes complementary to a selected sequence within the target sequence defined by the amplification region by the primers may be designed. In one exemplary example, oligonucleotide probes facilitating Real Time-PCR/qPCR product detection are complementary to a selected sequence within the target sequence downstream from either the upstream or downstream primer. Therefore, these probes hybridize to an internal sequence of the amplified fragment of a targeted sequence.

Many assays detecting the presence of a target can also quantify the amount of the target in a given sample. In particular, when there is only one copy of the identified strain specific genes, alleles thereof, or other allelic discriminative nucleic acid in a fungal genome, the primers and probes designed to specifically and selectively detect the presence or absence of such single copy target may be further used to quantify the amount of *Coccidioides* spp in a sample. In one embodiment, the *Coccidioides* quantification assay (or called CocciQuant assay hereafter) as provided herein is used to quantify the relative *Coccidioides* fungal load via ITS region specific to *Coccidioides*. In another embodiment, CocciQuant assay, combined with a *Coccidioides* discriminative assay (also called CocciDiff assay hereafter) detecting single copy target in a *Coccidioides* spp genome, is used to evaluate the copy number of ITS in a given *Coccidioides* isolate (for CocciDiff assay, see U.S. patent application Ser. No. 12/764,833, which is incorporated by reference herein in its entirety). In one embodiment, the CocciQuant assay as disclosed herein comprises primers CocciQuant-F (5'-CCTTCAAGCACGGCTTGTG-3', SEQ ID NO. 2) and CocciQuant-R (5'-CAGGCCCGTCCACACAAG-3', SEQ ID NO. 3). In another embodiment, a probe hybridized to the amplification products of the above primers may be included in the CocciQuant assay. In one embodiment, the probe may be 5'-TTGGGCYAACGTCC-3' (SEQ ID NO. 4). Further illustration of various aspects of the invention is detailed below.

II. Methods for Detecting *Coccidioides* Using Species Specific Sequences

Methods that can be used to identify strain specific nucleic acids, alleles of strain specific nucleic acids, and biomarkers derived from transcriptional and translational products of the strain specific nucleic acids and the alleles thereof, include PCR, Real Time-PCR, hybridization, sequencing and any combination of the above methods. In one embodiment, the presence of the PCR or Real Time-PCR products in an assay may indicate the presence of one or more *Coccidioides* strain(s). In one embodiment, the PCR or Real Time-PCR products may be further identified or differentiated by hybridization performed either simultaneously with or subsequently to the PCR reactions. In another embodiment, the PCR or Real Time-PCR products may be sequenced to ascertain the existence of a particular allele indicative of the identity of the one or more *Coccidioides* strains in a sample.

A nucleic acid may be added to a sample by any of a number of methods, including manual methods, mechanical methods, or any combination thereof. The presence of the allele may be signified by any of a number of methods, including amplification of a specific nucleic acid sequence, sequencing of a native or amplified nucleic acid, or the detection of a label either bound to or released from the nucleic acid. Addition of the nucleic acid to the sample also encompasses addition of the nucleic acid to a sample in which the target allele to which the nucleic acid has specificity is absent.

(a) PCR

Nucleic acids may be selectively and specifically amplified from a template nucleic acid contained in a sample. In some nucleic acid amplification methods, the copies are generated exponentially. Examples of nucleic acid amplification methods known in the art include: polymerase chain reaction (PCR), ligase chain reaction (LCR), self-sustained sequence replication (3SR), nucleic acid sequence based amplification (NASBA), strand displacement amplification (SDA), amplification with Qβ replicase, whole genome amplification with enzymes such as ϕ29, whole genome PCR, in vitro transcription with Klenow or any other RNA polymerase, or any other method by which copies of a desired sequence are generated.

With PCR, it is possible to amplify a single copy of a specific target sequence in genomic DNA to a level detectable by several different methodologies (for example, hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with an appropriate set of primer molecules. In particular, the amplified segments created by the PCR process itself are, themselves, efficient templates for subsequent PCR amplifications.

PCR generally involves the mixing of a nucleic acid sample, two or more primers that are designed to recognize the template DNA, a DNA polymerase, which may be a thermostable DNA polymerase such as Taq or Pfu, and deoxyribose nucleoside triphosphates (dNTP's). Reverse transcription PCR, quantitative reverse transcription PCR, and quantitative real time reverse transcription PCR are other specific examples of PCR. In general, the reaction mixture is subjected to temperature cycles comprising a denaturation stage (typically 80-100° C.), an annealing stage with a temperature that is selected based on the melting temperature (Tm) of the primers and the degeneracy of the primers, and an extension stage (for example 40-75° C.). In real-time PCR analysis, additional reagents, methods, optical detection systems, and devices known in the art are used that allow a measurement of the magnitude of fluorescence in proportion to concentration of amplified DNA. In such analyses, incorporation of fluorescent dye into the amplified strands may be detected or measured.

Alternatively, labeled probes that bind to a specific sequence during the annealing phase of the PCR may be used with primers. Labeled probes release their fluorescent tags during the extension phase so that the fluorescence level may be detected or measured. Generally, probes are complementary to a sequence within the target sequence downstream from either the upstream or downstream primer. Probes may include one or more label. A label may be any substance capable of aiding a machine, detector, sensor, device, or enhanced or unenhanced human eye from differentiating a labeled composition from an unlabeled composition. Examples of labels include but are not limited to: a radioactive isotope or chelate thereof, dye (fluorescent or nonfluorescent,) stain, enzyme, or nonradioactive metal. Specific examples include, but are not limited to: fluorescein, biotin, digoxigenin, alkaline phosphatese, biotin, streptavidin, $^{3}$H, $^{14}$C, $^{32}$P, $^{35}$S, or any other compound capable of emitting radiation, rhodamine, 4-(4'-dimethylamino-phenylazo)benzoic acid ("Dabcyl"); 4-(4'-dimethylamino-phenylazo)sulfonic acid (sulfonyl chloride) ("Dabsyl"); 5-(2-aminoethyl)-amino)-naphtalene-1-sulfonic acid ("EDANS"); Psoralene derivatives, haptens, cyanines, acridines, fluorescent rhodol derivatives, cholesterol derivatives; ethylenediaminetetraaceticacid ("EDTA") and derivatives thereof or any other compound that may be differentially detected. The label may also include one or more fluorescent dyes optimized for use in genotyping. Examples of dyes facilitating the reading of the target amplification include, but are not limited to: CAL-Fluor® Red 610, CAL-Fluor® Orange 560, dR110 (dichloro-substituted rhodamine 110), 5-FAM™ (5-carboxyfluorescein), 6FAM™ (6-carboxyfluorescein), dR6G (dichloro-substituted rhodamine 6G), JOE™ (4-5-dichloro-carboxyfluorescein), HEX™ (hexachloro-fluorescein), VIC®, TET™ (6-carboxy-1,4-dichloro-2',7'-dichloro-fluorescein), dTAMRA™ (dichloro-substituted carboxytetramethylrhodamine), TAMRA™ (carboxytetramethyl-rhodamine), NED™, dROX™ (dichloro-substituted 6-carboxyl-X-rhodamine), PET®, BHQ®, CAL-Fluor® Gold 540 (diisopropyl-phosphoramidous acid 2-cyano-ethyl ester 1-[2-(6-ethylamino-2,7-dimethyl-3-oxo-3H-xanthen-9-yl)-benzoyl]-piperidin-4-yl ester), and LIZ®.

Either primers or primers along with probes, as described above, will allow a quantification of the amount of specific template DNA present in the initial sample. In addition, RNA may be detected by PCR analysis by first creating a DNA template from RNA through a reverse transcriptase enzyme. In some aspects of the invention, the allele may be detected by quantitative PCR analysis facilitating genotyping analysis of the samples.

An illustrative example, using dual-labeled oligonucleotide probes in PCR reactions is disclosed in U.S. Pat. No. 5,716,784 to DiCesare. In the PCR step of the multiplex Real Time-PCR/PCR reaction of the present invention, the dual-labeled fluorescent oligonucleotide probe binds to the target nucleic acid between the flanking oligonucleotide primers during the annealing step of the PCR reaction. The 5' end of the oligonucleotide probe contains the energy transfer donor fluorophore (reporter fluor) and the 3' end contains the energy transfer acceptor fluorophore (quenching fluor). In the intact oligonucleotide probe, the 3' quenching fluor quenches the fluorescence of the 5' reporter fluor. However, when the oligonucleotide probe is bound to the target nucleic acid, the 5' to 3' exonuclease activity of the DNA polymerase, e.g., Taq DNA polymerase, will effectively digest the bound labeled oligonucleotide probe during the amplification step. Digestion of the oligonucleotide probe separates the 5' reporter fluor from the blocking effect of the 3' quenching fluor. The appearance of fluorescence by the reporter fluor is detected and monitored during the reaction, and the amount of detected fluorescence is proportional to the amount of fluorescent product released. Examples of apparatus suitable for detection include, e.g. Applied Biosystems™ 7900HT real-time PCR platform and Roche's 480 LightCycler, the ABI Prism 7700 sequence detector using 96-well reaction plates or GENEAMP PC System 9600 or 9700 in 9600 emulation mode followed by analysis in the ABA Prism Sequence Detector or TAQMAN LS-50B PCR Detection System. The labeled probe facilitated multiplex Real Time-PCR/PCR can also be performed in other real-time PCR systems with multiplexing capabilities.

"Amplification" is a special case of nucleic acid replication involving template specificity. Amplification may be a template-specific replication or a non-template-specific replication (in other words, replication may be specific template-dependent or not). Template specificity is here distinguished from fidelity of replication (in other words, synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

The term "template" refers to nucleic acid originating from a sample that is analyzed for the presence of a molecule of interest. In contrast, "background template" or "control" is used in reference to nucleic acid other than sample template that may or may not be present in a sample. Background template is most often inadvertent. It may be the result of carryover, or it may be due to the presence of nucleic acid contaminants sought to be purified out of the sample. For example, nucleic acids from organisms other than those to be detected may be present as background in a test sample.

Template specificity is achieved in most amplification techniques by the choice of enzyme. Amplification enzymes are enzymes that, under the conditions in which they are used, will process only specific sequences of nucleic acid in a heterogeneous mixture of nucleic acid. Other nucleic acid will not be replicated by this amplification enzyme. Similarly, in the case of T7 RNA polymerase, this amplification enzyme has a stringent specificity for its own promoters (Chamberlin et al. (1970) Nature (228):227). In the case of T4 DNA ligase, the enzyme will not ligate the two oligonucleotides or polynucleotides, where there is a mismatch between the oligonucleotide or polynucleotide substrate and the template at the ligation junction (Wu and Wallace (1989) Genomics (4):560). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.) (1989) PCR Technology, Stockton Press).

The term "amplifiable nucleic acid" refers to nucleic acids that may be amplified by any amplification method. It is contemplated that "amplifiable nucleic acid" will usually comprise "sample template."

The terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

In some forms of PCR assays, quantification of a target in an unknown sample is often required. Such quantification is often in reference to the quantity of a control sample. The control sample DNA may be co-amplified in the same tube in a multiplex assay or may be amplified in a separate tube. Generally, the control sample contains DNA at a known concentration. The control sample DNA may be a plasmid construct comprising only one copy of the amplification region to be used as quantification reference. To calculate the quantity of a target in an unknown sample, various mathematical models are established. Calculations are based on the comparison of the distinct cycle determined by various methods, e.g., crossing points (CP) and cycle threshold values (Ct) at a constant level of fluorescence; or CP acquisition according to established mathematic algorithm.

The algorithm for Ct values in Real Time-PCR calculates the cycle at which each PCR amplification reaches a significant threshold. The calculated Ct value is proportional to the number of target copies present in the sample, and the Ct value is a precise quantitative measurement of the copies of the target found in any sample. In other words, Ct values represent the presence of respective target that the primer sets are designed to recognize. If the target is missing in a sample, there should be no amplification in the Real Time-PCR reaction.

Alternatively, the Cp value may be utilized. A Cp value represents the cycle at which the increase of fluorescence is highest and where the logarithmic phase of a PCR begins. The LightCycler® 480 Software calculates the second derivatives of entire amplification curves and determines where this value is at its maximum. By using the second-derivative algorithm, data obtained are more reliable and reproducible, even if fluorescence is relatively low.

(b) Hybridization

In addition to PCR, genotyping analysis may also be performed using a probe that is capable of hybridizing to a nucleic acid sequence of interest. The term "hybridization" refers to the pairing of complementary nucleic acids. Hybridization and the strength of hybridization (i.e. the strength of the association between the nucleic acids) is impacted by such factors as the degree of complementary between the nucleic acids, stringency of the conditions involved, the Tm of the formed hybrid, and the G:C ratio within the nucleic acids. A single molecule that contains pairing of complementary nucleic acids within its structure is said to be "self-hybridized."

The terms "complementary" and "complementarity" refer to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" when used in relation to nucleic acids refers to a degree of complementarity. There may be partial homology, or complete homology and thus identical. "Sequence identity" refers to a measure of relatedness between two or more nucleic acids, and is given as a percentage with reference to the total comparison length. The identity calculation takes into account those nucleotide residues that are identical and in the same relative positions in their respective larger sequences. Calculations of identity may be performed by algorithms contained within computer programs such as "GAP" (Genetics Computer Group, Madison, Wis.) and "ALIGN" (DNAStar, Madison, Wis.). A partially complementary sequence, one that at least partially inhibits (or competes with) a completely complementary sequence from hybridizing to a target nucleic acid is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding, or hybridization, of a sequence that is completely homologous to a target under conditions of low stringency. This is not to say that conditions of low stringency are such that non-specific binding is permitted; low stringency conditions require that the binding of two sequences to one another be a specific and selective interaction. The absence of non-specific binding may be tested by the use of a second target which lacks even a partial degree of complementarity, for example, less than about 30% identity); in the absence of non-specific binding the probe will not hybridize to the second non-complementary target.

When used in reference to a double-stranded nucleic acid sequence such as a cDNA or genomic clone, the term "substantially homologous" refers to any probe which can hybridize to either or both strands of the double-stranded nucleic acid sequence under conditions of low stringency as described infra.

Low stringency conditions when used in reference to nucleic acid hybridization comprise conditions equivalent to binding or hybridization at 42° C. in a solution consisting of 5×SSPE (43.8 g/l NaC1, 6.9 g/l $NaH_2PO_4.H_2O$ and 1.85 g/l EDTA, pH adjusted to 7.4 with NaOH), 0.1% SDS, 5×Denhardt's reagent [50×Denhardt's contains per 500 ml: 5 g Ficoll (Type 400, Pharmacia), 5 g BSA (Fraction V; Sigma)] and 100 μg/ml denatured salmon sperm DNA followed by washing in a solution comprising 5×SSPE, 0.1% SDS at 42° C. when a probe of about 500 nucleotides in length is employed.

High stringency conditions when used in reference to nucleic acid hybridization comprise conditions equivalent to binding or hybridization at 42° C. in a solution consisting of 5×SSPE (43.8 g/l NaC1, 6.9 g/l $NaH_2PO_4.H_2O$ and 1.85 g/l EDTA, pH adjusted to 7.4 with NaOH), 0.5% SDS, 5×Denhardt's reagent and 100 μg/ml denatured salmon sperm DNA followed by washing in a solution comprising 0.1×SSPE, 1.0% SDS at 42° C. when a probe of about 500 nucleotides in length is employed.

It is well known that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components, for example, the presence or absence of formamide, dextran sulfate, polyethylene glycol, are considered and the hybridization solution may be varied to generate conditions of low stringency hybridization different from, but equivalent to, the above listed conditions. In addition, conditions are known in the art that promote hybridization under conditions of high stringency, for example, increasing the temperature of the hybridization and/or wash steps, the use of formamide in the hybridization solution, etc.

When used in reference to a double-stranded nucleic acid sequence such as a cDNA or genomic clone, the term "substantially homologous" refers to any probe that can hybridize to either or both strands of the double-stranded nucleic acid sequence under conditions of low to high stringency as described above.

When used in reference to a single-stranded nucleic acid sequence, the term "substantially homologous" refers to any probe that can hybridize, or is the complement of, the single-stranded nucleic acid sequence under conditions of low to high stringency as described above.

The term "Tm" refers to the "melting temperature" of a nucleic acid. The melting temperature is the temperature at which a population of double-stranded nucleic acid molecules becomes half dissociated into single strands. The equation for calculating the Tm of nucleic acids is well known in the art. As indicated by standard references, a simple estimate of the Tm value may be calculated by the equation: Tm=81.5+0.41(% G+C), when a nucleic acid is in aqueous solution at 1 M NaCl (See for example, Anderson and Young, Quantitative Filter Hybridization (1985) in Nucleic Acid Hybridization). Other references include more sophisticated computations that take structural as well as sequence characteristics into account for the calculation of Tm.

As used herein the term "stringency" refers to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "low" stringency are often required with nucleic acids that are derived from organisms that are genetically diverse, as the frequency of complementary sequences is usually less.

Probes for hybridization may comprise nucleic acids, oligonucleotides (DNA or RNA), proteins, protein complexes, conjugates, natural ligands, small molecules, nanoparticles, or any combination of molecules that includes one or more of the above, or any other molecular entity capable of specific binding to any allele, whether such molecular entity exists now or is yet to be disclosed. In one aspect of the invention, the probe comprises an oligonucleotide, as described herein.

Under some circumstances, methods of detecting a gene or an allele may involve assessing their expression level through their transcriptional or translational products such as a RNA or protein molecule. The expression of a gene or an allele may be assessed by any of a number of methods used currently in the art and yet to be developed. Examples include any nucleic acid detection method, including the following nonlimiting examples, microarray analysis, RNA in situ hybridization, RNAse protection assay, Northern blot. Other examples include any process of detecting expression that uses an antibody including the following nonlimiting examples, flow cytometry, immunohistochemistry, ELISA, Western blot, Northwestern blot, and immunoaffinity chromatograpy. Antibodies may be monoclonal, polyclonal, or any antibody fragment, for example, Fab, $F(ab)_2$, Fv, scFv, phage display antibody, peptibody, multispecific ligand, or any other reagent with specific binding to a target. Other methods of assessing protein expression include the following nonlimiting examples: HPLC, mass spectrometry, protein microarray analysis, PAGE analysis, isoelectric focusing, 2-D gel electrophoresis, and enzymatic assays.

In some aspects of the invention, the presence of an allele may be established by binding to probes in a media or on a microarray such as a DNA chip. Examples of DNA chips include chips in which a number of single stranded oligonucleotide probes are affixed to a solid substrate such as silicon glass. Oligonucleotides with a sequence complementary to an allele are capable of specifically binding to that allele to the exclusion of alleles that differ from the specific allele by one or more nucleotides. Labeled sample DNA is hybridized to the oligonucleotides and detection of the label is correlated with binding of the sample, and consequently, the presence of the allele in the sample.

In allele-specific hybridization, oligonucleotide sequences representing all possible variations at a polymorphic site are included on a chip. The chip and sample are subjected to conditions under which the labeled sample DNA will bind only to an oligonucleotide with an exact sequence match. In allele-specific primer extension, sample DNA hybridized to the chip may be used as a synthesis template with the affixed oligonucleotide as a primer. Under this method, only the added dNTP's are labeled. Incorporation of the labeled dNTP then serves as the signal indicating the presence of the allele. The fluorescent label may be detected by any of a number of instruments configured to read at least four different fluorescent labels on a DNA chip. In another alternative, the identity of the final dNTP added to the oligonucleotide may be assessed by mass spectrometry. In this alternative, the dNTP's may, but need not be labeled with a label of known molecular weight.

A nucleic acid probe may be affixed to a substrate. Alternatively, a sample may be affixed to the substrate. A probe or sample may be covalently bound to the substrate or it may be bound by some non covalent interaction including electrostatic, hydrophobic, hydrogen bonding, Van Der Waals, magnetic, or any other interaction by which a probe such as an oligonucleotide probe may be attached to a substrate while maintaining its ability to recognize the allele to which it has specificity. A substrate may be any solid or semi-solid material onto which a probe may be affixed, either singly or in the presence of one or more additional probes or samples as is exemplified in a microarray. Examples of substrate materials include but are not limited to polyvinyl, polysterene, polypropylene, polyester or any other plastic, glass, silicon dioxide or other silanes, hydrogels, gold, platinum, microbeads, micelles and other lipid formations, nitrocellulose, or nylon membranes. The substrate may take any form, including a spherical bead or flat surface. For example, the probe may be bound to a substrate in the case of an array or an in situ PCR reaction. The sample may be bound to a substrate in the case of a Southern Blot.

A nucleic acid probe may include a label. A label may be any substance capable of aiding 10 a machine, detector, sensor, device, or enhanced or unenhanced human eye from differentiating a labeled composition from an unlabeled composition. Examples of labels include, but are not limited to: a radioactive isotope or chelate thereof, dye (fluorescent or nonfluorescent,) stain, enzyme, or nonradioactive metal. Specific examples include, but are not limited to: fluorescein, biotin, digoxigenin, alkaline phosphatese, biotin, streptavidin, $^{3}H$, $^{14}C$, $^{32}P$, $^{35}S$, or any other compound capable of emitting radiation, rhodamine, 4-(4'-dimethylamino-phenylazo)benzoic acid ("Dabcyl"); 4-(4'-dimethylamino-phenylazo)sulfonic acid (sulfonyl chloride) ("Dabsyl"); 5-((2-aminoethyl)-amino)-naphtalene-1-sulfonicacid ("EDANS"); Psoralene derivatives, haptens, cyanines, acridines, fluorescent rhodol derivatives, cholesterol derivatives; ethylenediaminetetraaceticacid ("EDTA") and derivatives thereof, or any other compound that may be differentially detected. The label may also include one or more fluorescent dyes optimized for use in genotyping. Examples of such dyes include, but are not limited to: dR110 (dichloro-substituted rhodamine 110), 5-FAM™ (5-carboxyfluorescein), 6FAM™ (6-carboxyfluorescein), dR6G (dichloro-substituted rhodamine 6G), JOE™ (4-5-dichloro-carboxyfluorescein), HEX™ (hexachloro-fluorescein), VIC®, TET™ (6-carboxy-1,4-dichloro-2',7'-dichloro-fluorescein), dTAMRA™ (dichloro-substituted carboxytetramethylrhodamine), TAMRA™ (carboxytetramethylrhodamine), NED™, dROX™ (dichloro-substituted 6-carboxyl-X-rhodamine), PET®, BHQ®, CAL-Fluor® Gold 540 (diisopropyl-phosphoramidous acid 2-cyano-ethyl ester 1-[2-(6-ethylamino-2,7-dimethyl-3-oxo-3H-xanthen-9-yl)-benzoyl]-piperidin-4-yl ester), and LIZ®. Exemplary labels incorporated in probes in each assay are presented in TABLE B and Section I.

(c) Sequencing

Methods of detecting the presence of a gene or an allele further include, but are not limited to, any form of DNA sequencing including Sanger, next generation sequencing, pyrosequencing, SOLID sequencing, massively parallel sequencing, pooled, and barcoded DNA sequencing or any other sequencing method now known or yet to be disclosed; or any other method that allows the detection of a particular nucleic acid sequence within a sample or enables the differentiation of one nucleic acid from another nucleic acid that differs from the first nucleic acid by one or more nucleotides, or any combination of these.

In Sanger Sequencing, a single-stranded DNA template, a primer, a DNA polymerase, nucleotides and a label such as a radioactive label conjugated with the nucleotide base or a fluorescent label conjugated to the primer, and one chain terminator base comprising a dideoxynucleotide (ddATP, ddGTP, ddCTP, or ddTTP) are added to each of four reactions (one reaction for each of the chain terminator bases). The sequence may be determined by electrophoresis of the resulting strands. In dye terminator sequencing, each of the chain termination bases is labeled with a fluorescent label of a different wavelength which allows the sequencing to be performed in a single reaction.

In pyrosequencing, the addition of a base to a single stranded template to be sequenced by a polymerase results in the release of a phyrophosphate upon nucleotide incorporation. An ATP sulfurylase enzyme converts pyrophosphate into ATP which, in turn, catalyzes the conversion of luciferin to oxyluciferin which results in the generation of visible light that is then detected by a camera.

In SOLID sequencing, the molecule to be sequenced is fragmented and used to prepare a population of clonal magnetic beads, in which each bead is conjugated to a plurality of copies of a single fragment with an adaptor sequence, and alternatively, a barcode sequence. The beads are bound to a glass surface. Sequencing is then performed through 2-base encoding.

In massively parallel sequencing, randomly fragmented targeted DNA is attached to a surface. The fragments are extended and bridge amplified to create a flow cell with clusters, each with a plurality of copies of a single fragment sequence. The templates are sequenced by synthesizing the fragments in parallel. Bases are indicated by the release of a fluorescent dye correlating to the addition of the particular base to the fragment.

III Kits.

Kits that facilitate methods of detecting a strain or species specific sequence may include one or more of the following reagents: specific nucleic acids such as oligonucleotides, labeling reagents, enzymes including PCR amplification reagents such as the thermostable DNA polymerases Taq or Pfu, reverse transcriptase, or one or more other polymerases, and/or reagents that facilitate hybridization. Specific nucleic acids may include nucleic acids, polynucleotides, oligonucleotides (DNA, or RNA), or any combination of molecules that includes one or more of the above, or any other molecular entity capable of specific binding to a nucleic acid marker. In one aspect of the invention, the specific nucleic acid comprises one or more oligonucleotides capable of hybridizing to the marker.

A kit may also contain an indication that links the output of the kit to a particular result. For example, an indication may be one or more sequences or that signify the identification of a particular fungal phylum, class, order, family, genus species, subspecies, strain or any other delineation of a group of fungi. An indication may include a Ct value, wherein exceeding the Ct value indicates the presence or absence of an organism of interest. A kit may contain a positive control. A kit may contain a standard curve configured to quantify the amount of fungus present in a sample. An indication includes any guide that links the output of the kit to a particular result. The indication may be a level of fluorescence or radioactive decay, a value derived from a standard curve, or from a control, or any combination of these and other outputs. The indication may be printed on a writing that may be included in the kit or it may be posted on the Internet or embedded in a software package.

EXAMPLES

Various embodiments of the present teachings can be illustrated by the following nonlimiting examples. The following examples are illustrative, and are not intended to limit the scope of the claims.

Method and Material

Real Time Quantitative PCR (Real Time qPCR) was conducted in 384-well optical plates on Applied Biosystems 7900HT Real Time PCR System (Applied Biosystems, Carlsbad, Calif.; same thereafter). A 100 reaction volume was composed of 900 nM primers, 225 nM FAM-labeled hydrolysis probe, 1× Applied Biosystems TaqMan Universal PCR Master Mix, 1-2 μl template or sample DNA, and with molecular-grade water that brought the mixture to volume. Thermocycling included UNG treatment of 50° C. for 3 min, then Taq Polymerase activation of 95° C. for 10 min followed by 40 two-step cycles of 95° C. for 15 sec to denature DNA and 60° C. for 1 min for annealing and extension. Each reaction produced an amplification plot yielding a cycle-threshold (Ct) value directly proportional to the initial concentration of DNA in the reaction. Data were analyzed using Sequence Detection Systems version 2.3 to calculate target copies/20 and were exported in a text file, and numbers of ITS2 copies/genome were calculated in Microsoft Excel.

Example 1

*Coccidioides* Relative Quantification in a Sample Using CocciQuant Assay

CocciQuant assay is highly specific to *C. immitis* and *C. posadasii*. The assay detects the ITS region, a multi-copy target having the advantage of being detected at low levels in comparison a single-copy target. Although the copy number of ITS in *Coccidioides* isolates, including *C. immitis* and *C. posadasii*, varies, as disclosed herein, the average number of ITS copies in a *Coccidioides* genome is around 50 (see Table 7 below). Therefore, the CocciQuant assay detecting copy number of ITS region provides a method for relative quantification of *Coccidioides* fungal load.

Synthetic plasmid DNA was used to generate a standard curve for target copy number quantification. Two synthetic plasmids were made by Blue Heron Biotechnology (Bothell, Wash.). Each synthetic plasmid DNA included an ampicillin resistance gene, beta-lactamase (BLA) in the vector, one copy insert of ITS2, along with a copy of sequence containing an allelic discriminative SNP: W (Table 1, SEQ ID NO: 6). W is T in *C. immitis*, and W is A in *C. posadasii*. Therefore, one synthetic plasmid DNA comprises ITS2 and W=T, and the other synthetic plasmid DNA comprises ITS2 and W=A. A third plasmid was cloned in-house using TOPO TA 2.1 (Invitrogen, Carlsbad, Calif.) which included BLA in the vector and the ITS2 insert only (Table 1, SEQ ID NO: 5). The target of the allelic discrimination assay, CoccDiff was included for the purpose of testing the quantification assay's efficiency using previously developed primers and probes by the inventors.

TABLE 1

Sequence of in-house ITS2 only plasmid and of synthetic plasmid.

| Plasmid Name (Target) | Sequence | SEQ ID NO |
|---|---|---|
| ITS2 Plasmid (ITS2 Target only) | 5'TATAGGGCGATTGGGCCTCTAGATGCATGCTCGAGCGGCCGCCAGTGTGATGGAT ATCTGCAGAATTCGCCCTTGCATCATAGCAAAAATCAAACAAAACTTTCAACAACGGA TCTCTTGGTTCCGGCATCGATGAAGAACGCAGCGAAATGCGATAAGTAATGTGAATT GCAGAATTCCGTGAATCATCGAATCTTTGAACGCACATTGCGCCCTCTGGTATTCCGG GGGGCATGCCTGTTCGAGCGTCATTGCAAACCCTTCAAGCACGGCTTGTGTGTTGGG CTAACGTCCCCGCTTGTGTGGACGGGCCTGAAATGCAGTGGCGGCACCGAGTTCCTG GTGTCTGAGTGTATGGGAAATCACTTCATCGCTCAAAGACCCGATCGGGGCCGATCTT TTTTTTTTTATATCCGGTTTGACCTCGAAGGGCGAATTCCAGCACACTGGCGGCCGTT ACTAGTGGATCCGAGCTCGGTACCAAGCTTGGCGTAATCA3' | SEQ ID NO: 5 |
| Synthetic Plasmid (ITS2 + CocciDiff Targets; ITS2/W) W: *C. immitis* carries a T at this locus; *C. posadasii* carries A at this locus | 5'TCAGATTTACGCCGTAGCCTTTGATGGGCGACGGGTCGCCACTGGCAGCCTAGATA CGAGCGTGAGGATCTGGGATCCTCATWCTGGACAATGCCATGCTATACTGCAAGGCC ACACGTCCCTGCATCATAGCAAAAATCAAACAAAACTTTCAACAACGGATCTCTTGGT TCCGGCATCGATGAAGAACGCAGCGAAATGCGATAAGTAATGTGAATTGCAGAATTC CGTGAATCATCGAATCTTTGAACGCACATTGCGCCCTCTGGTATTCCGGGGGGCATGC CTGTTCGAGCGTCATTGCAAACCCTTCAAGCACGGCTTGTGTGTTGGGCCAACGTCCC CGCTTGTGTGGACGGGCCTGAAATGCAGTGGCGGCACCGAGTTCCTGGTGTCTGAGT GTATGGGAAATCACTTCATCGCTCAAAGACC3' | SEQ ID NO: 6 |

Genome DNA concentration of all plasmids was quantified and subsequently normalized to $10^8$ copies/20 using an in-house qPCR assay, which targets the BLA gene (a single copy gene in the reference plasmid). The method of normalizing DNA concentration to DNA copy number per unit solution is known in the art. Using the BLA gene as a DNA copy number reference, standard sample sets comprising ten-fold serial DNA dilutions ranging from $10^8$ copies/20 to 10 copies/20 of a synthetic plasmid DNA were prepared. A standard curve was then developed using the standard sample sets with each dilution tested in three reactions via Quantitative PCR (qPCR) comprising primer sets: CocciQuant-F (5'-CCT-TCAAGCACGGCTTGTG-3', SEQ ID NO. 2) and Cocci-Quant-R (5'-CAGGCCCGTCCACACAAG-3', SEQ ID NO. 3). CocciQuant probe (5'-TTGGGCYAACGTCC-3'; SEQ ID NO: 4) may be further used in the CocciQuant assay comprising SEQ ID NO. 2 and SEQ ID NO. 3 for a better result in quantifying the amplification products. CocciQuant probe is a degenerative probe, with Y being T or C. Since it was found that *Coccidioides* isolates, including *C. immitis* and *C. posadasii*, has either T or C at this locus, using SEQ ID NO: 4 as a probe is able to detect total *Coccidioides* in a sample.

Figure 2:
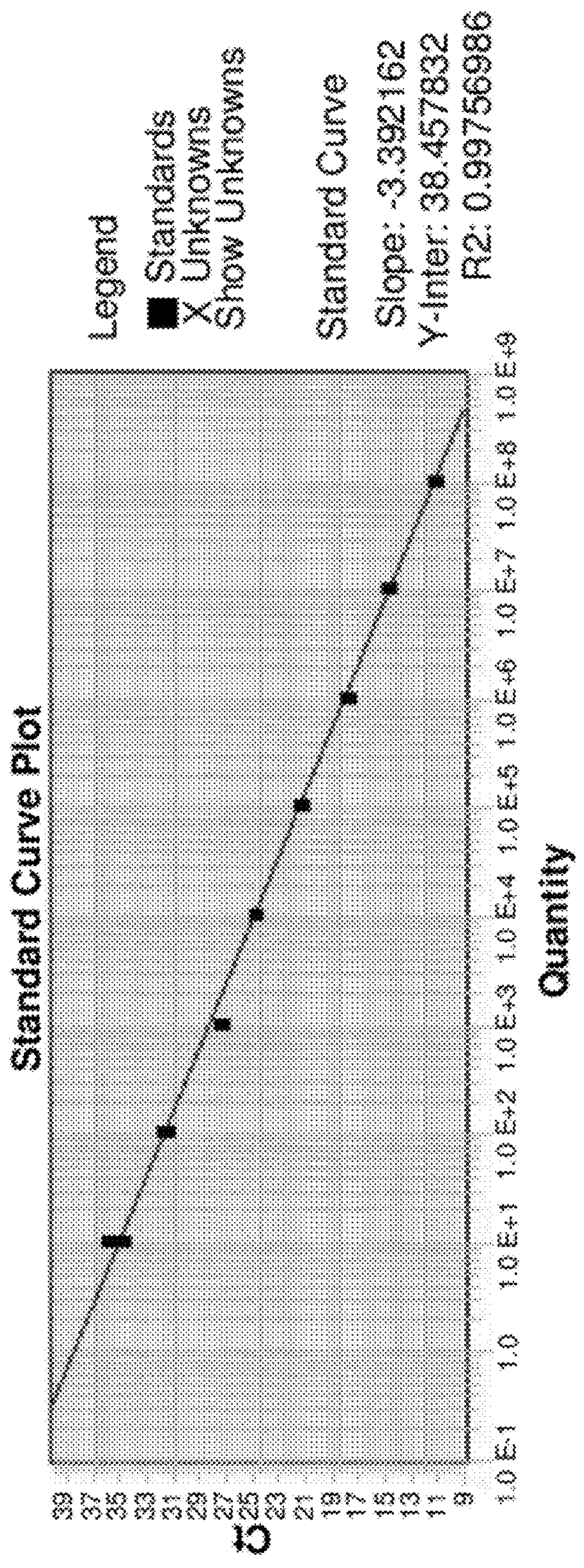
FIG. 2 depicts the linear/log regression of a standard curve derived from a typical standard set in FIG. 1.

FIG. 1 provided a combined amplification plot resulting from qPCR using each dilution in the standard sample sets. The qPCR results in the form of amplification fluorescence signal intensity versus PCR cycle numbers in FIG. 1 were further used to generate a standard curve plot using a log-linear regression of cycle threshold value versus plasmid concentration described by the number of target copies per 2 μl sample. As shown in FIG. 2, the log-linear regression of cycle threshold (Ct) value was used to obtain the copy number of the ITS region of *Coccidioides* in unknown samples. Alternatively, Formula I describing the standard curve by log-linear regression can be used to calculate ITS copy number using Ct value:

$$\text{ITS copy number in unknown sample}=10^{[(Ct-Y\text{-}intercept)/slope]} \qquad \text{[Formula I]}$$

In this example, a set of standard sample sets and an unknown sample were subjected to the CocciQuant assay, the Y-intercept value of the standard curve for this particular qPCR was 38.46, and the Slope was −3.39. With the Ct value for the unknown sample being 15, after applying these parameters to the above Formula I, the ITS copy number of all *Coccidioides* in this unknown sample is:

$$\text{Quantity}=10^{[(15-38.46)/-3.39]}=8.32\times10^{6} \text{ copies of ITS}$$

Table 2 presented more exemplary DNA copy number quantification in unknown clinical specimens using Cocci-Quant assay.

TABLE 2

ITS copy number for unknown clinical specimens

| Clinical Specimen ID | Ct | Calculated Quantity (copies/μl) |
|---|---|---|
| TG10192 | 38.9 | 7.17E−01 |
| TG10194 | 39.0 | 6.91E−01 |
| TG12498 | 39.0 | 6.99E−01 |
| TG10190 | 38.1 | 1.26E+00 |
| TG11439 | 22.9 | 3.97E+04 |
| TG11438 | 35.3 | 8.77E+00 |
| TG11443 | 39.9 | 3.81E−01 |
| TG11444 | 33.9 | 2.24E+01 |
| TG11445 | 28.9 | 6.54E+02 |
| TG11446 | 39.6 | 4.49E−01 |
| TG11447 | 29.5 | 4.39E+02 |
| TG10197 | 30.4 | 2.42E+02 |

TABLE 2-continued

ITS copy number for unknown clinical specimens

| Clinical Specimen ID | Ct | Calculated Quantity (copies/μl) |
|---|---|---|
| TG11448 | 39.0 | 6.70E−01 |
| TG11449 | 32.2 | 6.94E+01 |
| TG11451 | 21.1 | 1.35E+05 |

Example 2

Specificity of CocciQuant Assay

To further illustrate the specificity of CocciQuant assay, the assay was tested against a number of differential diagnostic isolates and near neighbor or background isolates. All assay results were negative (see Table 3 and Table 4), indicating the sample species doesn't contain *C. immitis* and *C. posadasii* specific sequence amplifiable using CocciQuant assay comprising CocciQuant-F (SEQ ID NO: 2) and CocciQuant-BD-R (SEQ ID NO: 3) primer set.

TABLE 3

The assay was tested against the following differential diagnostic isolates. All were negative.

| Species | Total number screened |
|---|---|
| *Abiotrophia granulicattella* | 1 |
| *Acinetobacter baumanni* | 1 |
| *Acromobacter xylosoxidans* | 1 |
| *Bacillus* spp. | 2 |
| *Bacteroides fragilis* | 1 |
| *Bacteroides uniformis* | 1 |
| *Bordetella bronchiseptica* | 1 |
| *Burkholderia cepacia* | 1 |
| *Burkholderia psuedomallei* | 3 |
| *Candida albicans* | 1 |
| *Candida glabrata* | 2 |
| *Candida parapsilosis* | 3 |
| *Candida tropicalis* | 1 |
| *Chryseobacterium indologenes* | 1 |
| *Corynebacterium* spp. | 1 |
| *Coxiella burnetii* | 2 |
| *Enterobacter aerogenes* | 2 |
| *Enterobacter cloacae* | 9 |
| *Enterococcus faecium* | 2 |
| *Enterococcus* sp | 2 |
| *Francisella tulerensis* | 2 |
| Group F *Streptococcus* | 1 |
| *Haemophilus parainfluenza* | 2 |
| Human gDNA | 2 |
| *Legionella pneumophila* | 1 |
| *Listeria monocytogenes* | 1 |
| *Micrococcus* spp. | 1 |
| *Neisseria meningitidis* | 3 |
| *Neisseriea gonorrhoeae* | 3 |
| *Propionibacterium* spp. | 1 |
| *Providencia stuartii* | 1 |
| *Staphylococcus aureus* | 4 |
| *Staphylococcus epidermidis* | 5 |
| *Staphylococcus saprophyticus* | 1 |
| *Streptococcus agalactiae* | 1 |
| *Streptococcus mitis* | 1 |
| *Streptococcus pnuemoniae* | 3 |
| *Streptococcus pyogenes* | 3 |
| *Streptococcus salivarius* | 1 |
| *Streptococcus viridans* | 3 |
| Unspeciated-CNS | 6 |
| Vancomycin Resistant *Enterococcus* | 8 |

TABLE 3-continued

| The assay was tested against the following differential diagnostic isolates. All were negative. | |
|---|---|
| Species | Total number screened |
| Vancomycin Resistant *Staphylococcus* | 6 |
| Vancomycin Sensitive *Enterococcus* | 2 |

TABLE 4

| The assay was tested against the following near neighbor and background isolates. All were negative. | |
|---|---|
| Near-Neighbor and Background Isolates | *Uncinocarpus reesii*<br>*Histoplama capsulatum*<br>*Homo sapiens* |

Example 3

Sensitivity and Efficiency of CocciQuant Assay (1) Determining Limit of Detection Also called the Detection Limit, Lower Limit of Detection, or Limit of Detection (LOD), is the lowest quantity of a substance that can be distinguished from the absence of that substance (i.e. a blank value) within a stated confidence limit. LOD is hereby used to describe the sensitivity of CocciQuant assay. Samples comprising DNA of synthetic plasmid having ITS2 were quantified, and limiting serial dilutions were created to test the Limit of Detection. Dilutions were queried across the CocciQuant assay with 20 replicates each. Finally, to establish the LOD, dilutions for which at least 19 of 20 replicates amplified were further evaluated by testing 64 replicates and exhibited at least 95% amplification (61/64 amplification ratio) as a confidence limit. Results shown in Table 5 demonstrated that the LOD of ITS2 detection using CocciQuant assay is 5 copies/2 μl. If the copy number/2 μl in a sample is lower than 5, the CocciQuant assay may not be sensitive enough to either reliably detect the presence or absence of the target, nor a reliable calculation of the copy number of a target DNA in the sample. Therefore, CocciQuant assay, targeting a multi-copy region that is around 50 copies in an isolate, has a warranted sensitivity and accuracy in evaluating the relative fungal load via ITS copy number.

TABLE 5

Determine CocciQuant Limit of Detection:

| ITS2 Target Copies/2 μl | Initial Screening | Confirmation of LOD | Mean Ct | Limit of Detection (LoD) of ITS2 Target (Copies/2 μl) |
|---|---|---|---|---|
| 50 | 20/20 | N/A | 32.61 | 5 copies/2 ul |
| 25 | 20/20 | N/A | 33.69 | (Ct = 35.86) |
| 10 | 20/20 | N/A | 35.16 | |
| 5 | 19/20 | 63/64 | 35.86 | |

(2) Coefficient of Determination

Further Coefficient of Determination ($R^2$) is used to provide a measure of how well future outcomes are likely to be predicted by a statistical model such as the one provided by Formula I, herein, the CocciQuant assay. In the context of linear regression, $R^2$ is the square of the sample correlation coefficient (or efficiency) between the outcomes and their predicted values (Table 6 and Formula II and III).

Assay efficiency $R=10^{(-1/m)}-1$;

where $m$=slope of the standard curve. [Formula II]

Coefficient of determination=$R^2$ [Formula III]

The coefficient of determination of the regression based on CocciQuant assay was 0.998.

TABLE 6

CocciQuant and CocciDiff assay efficiencies

| Assay | Synthetic Plasmid Template (by CocciDiff Target Species) | Slope | Y-intercept | $R^2$ | Efficiency |
|---|---|---|---|---|---|
| CocciQuant | *C. posadasii* | −3.34 | 37.12 | 0.9997 | 0.99 |
| | *C. immitis* | −3.27 | 36.79 | 0.9993 | 1.02 |
| CocciDiff | *C. posadasii* | −3.57 | 40.40 | 0.9997 | 0.90 |
| | *C. immitis* | −3.57 | 40.11 | 0.9992 | 0.91 |

Example 4

ITS2 Copy Number Per Genome of *Coccidioides* Isolates

As provided herein, CocciQuant targets the ITS2, a multi-copy region in *Coccidioides* genome. Also provided is the sequence of SEQ ID NO: 1, a single copy region in *Coccidioides* genome, comprising an allelic discriminative W locus. CocciDiff is an assay used to determine if a sample contains one of the two Cocci species: *C. immitis* or *C. posadasii* (U.S. patent application Ser. No. 12/764,833, incorporated by reference herein in its entirety). Because CocciDiff target is a single copy in the *Coccidioides* genome, it was used as a reference for CocciQuant assay in evaluating ITS2 copy number per genome in a given *Coccidioides* isolate.

*Coccidioides* isolates were tested across CocciQuant and CocciDiff (Forward primer: 5'-CGTGTGGCCTTGCAGTATAGC-3' SEQ ID NO: 7; Reverse primer: 5'-TTTACGCCGTAGCCTTTGATG-3' SEQ ID NO: 8; Probe: 5'-GATCCTCATWCTGGACAA-3' W=T or A, SEQ ID NO: 9). The Ct value of CocciQuant assay was used to determine the total copy number of the ITS2 region in the sample (see Example 1 and Formula I); whereas the Ct value of CocciDiff assay correlates to the number of genomes in the sample due to the single copy nature of the target. The relative Ct value or the difference in copy number quantities between CocciDiff and CocciQuant produced by the combined assay was used to calculate copy number of ITS2 per genome (Formula IV).

ITS2 Copy Number=[CQ Mean Quantity−(CD Mean Quantity*1.1)]/[CD Mean Quantity*1.1]

Where CQ=CocciQuant Copies/μl;CD=CocciDiff Copies/μl [Formula IV]

As shown in Table 6, the number of ITS copies/genome in *C. immitis* or *C. posadasii* is averagely around 50, with one tested isolate being most likely an abnormality due to yet identified reason.

TABLE 6

| Coccidioides ITS2 Copies/Genome: | | | | | |
|---|---|---|---|---|---|
| Isolate | CocciQuant Copies/μl Mean | CocciQuant Copies/μl SD | CocciDiff Copies/μl Mean | CocciDiff Copies/μl SD | ITS2 copies/genome |
| *Immitis* 1 | 2.37E+06 | 9.20E+05 | 7.65E+05 | 8.48E+04 | 2 |
| *Immitis* 2 | 2.24E+08 | 5.38E+07 | 3.35E+06 | 3.59E+05 | 60 |
| *Immitis* 3 | 6.33E+07 | 1.56E+07 | 1.36E+06 | 1.41E+05 | 41 |
| *Posadasii* 1 | 8.98E+07 | 1.95E+07 | 1.61E+06 | 1.22E+05 | 50 |
| *Posadasii* 2 | 9.36E+07 | 1.29E+07 | 1.38E+06 | 2.37E+05 | 61 |
| *Posadasii* 3 | 7.20E+07 | 5.93E+06 | 1.34E+06 | 4.20E+05 | 48 |

Example 5

Detecting *Coccidioides* in Clinical Specimens Using CocciQuant

CocciQuant uses oligonucleotides including primers (SEQ ID NO. 2 and SEQ ID NO. 3), and probe (SEQ ID NO. 4). In Table 7, the shaded samples are those that tested positive by Gen-Probe DNA probe (Gen-Probe, San Diego, Calif.), which identifies *Coccidioides* isolated from culture. Note that TG11438, TG11444, TG11447 (labeled with "*"), were negative on the DNA probe, yet still positive by CocciQuant, and the CocciDiff quantitative PCR.

TABLE 7

| Sample ID | Type | Cocci Gen-Probe | Cocci infection status | CocciQuant TG | CocciDiff |
|---|---|---|---|---|---|
| TG10192 | BAL | NA | NA | 38.3 | UD |
| TG10194 | Sputum | NA | NA | 37.9 | UD |
| TG12498 | Sputum | NA | NA | 39.0/UD | UD |
| TG10193 | Sputum | NA | NA | UD | UD |

TABLE 7-continued

| Sample ID | Type | Cocci Gen-Probe | Cocci infection status | CocciQuant TG | CocciDiff |
|---|---|---|---|---|---|
| TG10191 | Sputum | NA | NA | 36.0/UD | UD |
| TG10190 | Sputum | NA | NA | 37.4 | UD |
| TG11439 | BAL | POS | Active | 22.0 | *C. posadasii* |
| TG11438 | BAL | NA* | NA | 34.4* | *C. posadasii** |
| TG10199 | BAL | NA | NA | UD | UD |
| TG11440 | BAL | NA | NA | 36.9/UD | UD |
| TG10195 | Sputum | NA | NA | 36.5/UD | UD |
| TG11441 | BAL | NA | NA | 37.4/UD | UD |
| TG11442 | BAL | NA | NA | UD | UD |
| TG11443 | BAL | NA | NA | 39.4 | UD |
| TG10198 | BAL | NA | NA | UD | UD |
| TG11444 | BAL | NA* | NA | 32.9* | *C. posadasii** |
| TG11445 | BAL | POS | Active | 28.2 | *C. posadasii* |
| TG11446 | Sputum | NA | NA | 39.6/UD | UD |
| TG11447 | BAL | NA* | NA | 28.8* | *C. posadasii** |
| TG10197 | BAL | POS | Active | 29.6 | *C. posadasii* |
| TG11448 | BAL | NA | Active | 37.8 | UD |
| | Tissue bx | POS | Dormant | 31.2 | *C. posadasii* |
| TG11449 | BAL | POS | ACTIVE | UD | *C. posadasii* |
| TG11450 | BAL | NA | NA | UD | UD |
| TG11451 | Sputum | POS | ACTIVE | 20.0 | *C. posadasii* |
| TG10196 | Sputum | NA | NA | UD | UD |

We claim:

1. A method of determining the presence or absence of *Coccidioides* in a DNA-containing sample comprising the steps of:
   - adding a first oligonucleotide capable of binding SEQ ID NO. 5 or to a complement of SEQ ID NO. 5 to a mixture comprising the DNA-containing sample, wherein the first oligonucleotide comprises SEQ ID NO. 2;
   - adding a second oligonucleotide that is capable of hybridizing with complements of SEQ ID NO. 3 to the mixture;
   - adding a third oligonucleotide to the mixture;
   - subjecting the mixture to conditions that allow amplification of nucleic acid, wherein the third oligonucleotide binds to its complement included in the amplification products of the first and second oligonucleotides;
   - wherein at least one of the first and the second oligonucleotides comprises a label;
   - obtaining a result indicating whether or not nucleic acid amplification has occurred;
   - and determining the presence or absence of *Coccidioides* in the DNA-containing sample based on the result.

2. The method of claim 1, wherein the result comprises a Ct value.

3. The method of claim 1, wherein the third oligonucleotide includes SEQ ID NO. 4.

4. The method of claim 1, wherein the label comprises a fluorescent label selected from the group consisting of fluorescein, dichloro-substituted rhodamine 110, 5-carboxyfluorescein, 6-carboxyfluorescein, dichloro-substituted rhodamine 6G, 4-5-dichloro-carboxyfluorescein, hexachloro-fluorescein, 6 carboxy-1,4-dichloro-2',7'-dichloro-fluorescein, dichloro-substituted carboxytetramethylrhodamine, carboxytetramethylrhodamine, dichloro-substituted 6-carboxyl-X-rhodamine, and diisopropyl-phosphoramidous acid 2-cyano-ethyl ester 1-[2-(6-ethylamino-2,7-dimethyl-3-oxo-3H-xanthen-9-yl)-benzoyl]-piperidin-4-yl ester.

5. The methods of claim 4, wherein the third oligonucleotide comprises a fluorescent label selected from the group consisting of fluorescein, dichloro-substituted rhodamine 110, 5-carboxyfluorescein, 6-carboxyfluorescein, dichloro-substituted rhodamine 6G, 4-5-dichloro-carboxyfluorescein, hexachloro-fluorescein, 6-carboxy-1,4-dichloro-2',7'-dichloro-fluorescein, dichloro-substituted carboxytetramethylrhodamine, carboxytetramethylrhodamine, dichloro-substituted 6-carboxyl-X-rhodamine, and diisopropyl-phosphoramidous acid 2-cyano-ethyl ester 1-[2-(6-ethylamino-2,7-dimethyl-3-oxo-3H-xanthen-9-yl)-benzoyl]-piperidin-4-yl ester.

6. The method of claim 1, further comprising the step of isolating DNA from the DNA-containing sample.

7. The method of claim 1, wherein the sample comprises an environmental sample.

8. The method of claim 1, wherein the sample is derived from a subject.

9. The method of claim 8, wherein the subject is selected from the group consisting of a human, a companion animal, and a livestock animal.

10. A method of quantifying *Coccidioides* in a DNA-containing sample comprising the steps of:

adding a first and a second oligonucleotide capable of binding SEQ ID NO. 5 or to a complement of SEQ ID NO. 5 to a first mixture comprising the DNA-containing sample, wherein the first oligonucleotide differs from the second oligonucleotide;

adding a fourth and fifth oligonucleotide to a second mixture comprising nucleic acid having SEQ ID NO. 1 or SEQ ID NO. 6, wherein the fourth and fifth oligonucleotides differ from one another and wherein the fourth oligonucleotide includes SEQ ID NO: 7 and wherein the fifth oligonucleotide includes SEQ ID NO: 8;

subjecting the first and the second mixture to conditions that allow nucleic acid amplification;

receiving a first result from said nucleic amplification of said first mixture and a second result from said nucleic amplification of said second mixture;

and comparing said first result with said second result to thereby quantify *Coccidioides*.

11. The method of claim 10, wherein the first and the second results each comprise a Ct value.

12. The method of claim 10, wherein the first oligonucleotide is capable of hybridizing with complements of SEQ ID NO. 3, and the second oligonucleotide is capable of hybridizing with complements of SEQ ID NO. 2, under stringent conditions.

13. The method of claim 12, further comprising the step of adding a third oligonucleotide to the mixture, wherein the third oligonucleotide binds to its complement included in the amplification products of the first and second oligonucleotides.

14. The method of claim 13, wherein the third oligonucleotide includes SEQ ID NO. 4.

15. The method of claim 10, wherein at least one of the first and the second oligonucleotides comprises a label.

16. The method of claim 15, wherein the label comprises a fluorescent label selected from the group consisting of fluorescein, dichloro-substituted rhodamine 110, 5-carboxyfluorescein, 6-carboxyfluorescein, dichloro-substituted rhodamine 6G, 4-5-dichloro-carboxyfluorescein, hexachloro-fluorescein, 6 carboxy-1,4-dichloro-2',7'-dichloro-fluorescein, dichloro-substituted carboxytetramethylrhodamine, carboxytetramethylrhodamine, dichloro-substituted 6-carboxyl-X-rhodamine, and diisopropyl-phosphoramidous acid 2-cyano-ethyl ester 1-[2-(6-ethylamino-2,7-dimethyl-3-oxo-3H-xanthen-9-yl)-benzoyl]-piperidin-4-yl ester.

17. The method of claim 14, wherein the third oligonucleotide comprises a fluorescent label selected from the group consisting of fluorescein, dichloro-substituted rhodamine 110, 5-carboxyfluorescein, 6-carboxyfluorescein, dichloro-substituted rhodamine 6G, 4-5-dichloro-carboxyfluorescein, hexachloro-fluorescein, 6-carboxy-1,4-dichloro-2',7'-dichloro-fluorescein, dichloro-substituted carboxytetramethylrhodamine, carboxytetramethylrhodamine, dichloro-substituted 6-carboxyl-X-rhodamine, and diisopropyl-phosphoramidous acid 2-cyano-ethyl ester 1-[2-(6-ethylamino-2,7-dimethyl-3-oxo-3H-xanthen-9-yl)-benzoyl] piperidin-4-yl ester.

18. The method of claim 10, further comprising the step of isolating DNA from the DNA-containing sample.

19. The method of claim 10, wherein the sample comprises an environmental sample.

20. The method of claim 10, wherein the sample is derived from a subject.

21. The method of claim 20, wherein the subject is selected from the group consisting of a human, a companion animal, and a livestock animal.

* * * * *

SEQUENCE LISTING

```
<160> NUMBER OF SEQ ID NOS: 9

<210> SEQ ID NO 1
<211> LENGTH: 58
<212> TYPE: DNA
<213> ORGANISM: Coccidioides immitis
<220> FEATURE:
<221> NAME/KEY: misc_feature
<222> LOCATION: (29)..(29)
<223> OTHER INFORMATION: w=t or a

<400> SEQUENCE: 1

cccttcaagc acggcttgtg tgttgggcwa acgtcccccg cttgtgtgga cgggcctg        58


<210> SEQ ID NO 2
<211> LENGTH: 19
<212> TYPE: DNA
<213> ORGANISM: Artificial Sequence
<220> FEATURE:
<223> OTHER INFORMATION: DNA CocciQuant Forward Primer

<400> SEQUENCE: 2

ccttcaagca cggcttgtg                                                   19
```

-continued

<210> SEQ ID NO 3
<211> LENGTH: 18
<212> TYPE: DNA
<213> ORGANISM: Artificial Sequence
<220> FEATURE:
<223> OTHER INFORMATION: DNA CocciQuant Reverse Primer

<400> SEQUENCE: 3
caggcccgtc cacacaag 18

<210> SEQ ID NO 4
<211> LENGTH: 14
<212> TYPE: DNA
<213> ORGANISM: Artificial Sequence
<220> FEATURE:
<223> OTHER INFORMATION: DNA Cocciquant probe
<220> FEATURE:
<221> NAME/KEY: misc_feature
<222> LOCATION: (7)..(7)
<223> OTHER INFORMATION: y is t or c

<400> SEQUENCE: 4
ttgggcyaac gtcc 14

<210> SEQ ID NO 5
<211> LENGTH: 498
<212> TYPE: DNA
<213> ORGANISM: Artificial Sequence
<220> FEATURE:
<223> OTHER INFORMATION: ITS2 plasmid insert

<400> SEQUENCE: 5
tatagggcga ttgggcctct agatgcatgc tcgagcggcc gccagtgtga tggatatctg 60
cagaattcgc ccttgcatca tagcaaaaat caaacaaaac tttcaacaac ggatctcttg 120
gttccggcat cgatgaagaa cgcagcgaaa tgcgataagt aatgtgaatt gcagaattcc 180
gtgaatcatc gaatctttga acgcacattg cgccctctgg tattccgggg ggcatgcctg 240
ttcgagcgtc attgcaaacc cttcaagcac ggcttgtgtg ttgggctaac gtccccgctt 300
gtgtggacgg gcctgaaatg cagtggcggc accgagttcc tggtgtctga gtgtatggga 360
aatcacttca tcgctcaaag acccgatcgg ggccgatctt ttttttttta tatccggttt 420
gacctcgaag ggcgaattcc agcacactgg cggccgttac tagtggatcc gagctcggta 480
ccaagcttgg cgtaatca 498

<210> SEQ ID NO 6
<211> LENGTH: 432
<212> TYPE: DNA
<213> ORGANISM: Artificial Sequence
<220> FEATURE:
<223> OTHER INFORMATION: ITS2/W plasmid insert
<220> FEATURE:
<221> NAME/KEY: misc_feature
<222> LOCATION: (83)..(83)
<223> OTHER INFORMATION: w=t or a

<400> SEQUENCE: 6
tcagatttac gccgtagcct ttgatgggcg acgggtcgcc actggcagcc tagatacgag 60
cgtgaggatc tgggatcctc atwctggaca atgccatgct atactgcaag gccacacgtc 120
cctgcatcat agcaaaaatc aaacaaaact ttcaacaacg gatctcttgg ttccggcatc 180
gatgaagaac gcagcgaaat gcgataagta atgtgaattg cagaattccg tgaatcatcg 240
aatctttgaa cgcacattgc gccctctggt attccggggg gcatgcctgt tcgagcgtca 300

-continued

```
ttgcaaaccc ttcaagcacg gcttgtgtgt tgggccaacg tccccgcttg tgtggacggg    360

cctgaaatgc agtggcggca ccgagttcct ggtgtctgag tgtatgggaa atcacttcat    420

cgctcaaaga cc                                                        432


<210> SEQ ID NO 7
<211> LENGTH: 21
<212> TYPE: DNA
<213> ORGANISM: Artificial Sequence
<220> FEATURE:
<223> OTHER INFORMATION: CocciDiff Forward primer

<400> SEQUENCE: 7

cgtgtggcct tgcagtatag c                                               21


<210> SEQ ID NO 8
<211> LENGTH: 21
<212> TYPE: DNA
<213> ORGANISM: Artificial Sequence
<220> FEATURE:
<223> OTHER INFORMATION: CocciDiff Reverse primer

<400> SEQUENCE: 8

tttacgccgt agcctttgat g                                               21


<210> SEQ ID NO 9
<211> LENGTH: 18
<212> TYPE: DNA
<213> ORGANISM: Artificial Sequence
<220> FEATURE:
<223> OTHER INFORMATION: CocciDiff primer
<220> FEATURE:
<221> NAME/KEY: misc_feature
<222> LOCATION: (10)..(10)
<223> OTHER INFORMATION: w=t or a

<400> SEQUENCE: 9

gatcctcatw ctggacaa                                                   18
```